United States Patent
Iwai et al.

(10) Patent No.: US 7,830,502 B2
(45) Date of Patent: Nov. 9, 2010

(54) SUBSTRATE INSPECTION DEVICE AND SUBSTRATE INSPECTION METHOD

(75) Inventors: Susumu Iwai, Saitama (JP); Noboru Kato, Saitama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/540,825

(22) Filed: Aug. 13, 2009

(65) Prior Publication Data

US 2010/0060889 A1    Mar. 11, 2010

(30) Foreign Application Priority Data

Sep. 8, 2008    (JP) .............................. 2008-230203

(51) Int. Cl.
*G01N 21/88* (2006.01)

(52) U.S. Cl. ................................. 356/237.5; 356/237.4

(58) Field of Classification Search ... 356/237.1–237.5, 356/394; 250/559.4, 559.41, 559.46, 341.1
See application file for complete search history.

(56) References Cited

U.S. PATENT DOCUMENTS

| | | | | |
|---|---|---|---|---|
| 4,760,265 A | * | 7/1988 | Yoshida et al. | ........... 250/492.2 |
| 5,149,982 A | * | 9/1992 | Hagiwara et al. | ...... 250/559.41 |
| 6,399,957 B1 | * | 6/2002 | Murata | ..................... 250/559.4 |
| 6,710,868 B2 | * | 3/2004 | Guetta | ...................... 356/237.1 |
| 6,724,005 B2 | * | 4/2004 | Tokumoto | ................ 250/559.4 |

FOREIGN PATENT DOCUMENTS

| | | | |
|---|---|---|---|
| JP | 2005-164558 | | 6/2005 |
| JP | 2006194755 A | * | 7/2006 |

* cited by examiner

*Primary Examiner*—Sang Nguyen
(74) *Attorney, Agent, or Firm*—J.C. Patents

(57) ABSTRACT

A substrate inspection method includes the following steps. Substrates are sequentially moved while an optical system including a light-projecting system and a light-receiving system are moved in a direction orthogonal to the moving direction of each substrate, so as to change the scanned area of each substrate which is scanned with an inspection light having a specific width in the direction orthogonal to the moving direction of the substrate from the light-projecting system; data of the inspected defects of the substrates in the scanned areas are stored for each scanned area; and the stored data of the defects of the substrates in the scanned areas are updated with newly inspected data of the defects of the substrates in the same scanned areas for each substrate, and defect data of one substrate are produced based on the data of the defects of the substrates in a plurality of scanned areas.

4 Claims, 8 Drawing Sheets

SUBSTRATE INSPECTION DEVICE AND SUBSTRATE INSPECTION METHOD

CROSS-REFERENCE TO RELATED APPLICATION

This application claims the priority benefit of Japan application serial no. 2008-230203, filed on Sep. 8, 2008. The entirety of the above-mentioned patent application is hereby incorporated by reference herein and made a part of specification.

BACKGROUND OF THE INVENTION

1. Field of Invention

The present invention relates to a substrate inspection device and a substrate inspection method for inspecting a manufactured glass or plastic substrate used for a display panel, and particularly to a substrate inspection device and a substrate inspection method for inspecting defect on a substrate in a production line of a glass or plastic substrate or in a production line of a display panel substrate using the glass or plastic substrate.

2. Description of Related Art

A thin film transistor (TFT) substrate, a color filter substrate for a display panel of a liquid crystal display device, a substrate for a plasma display panel or a substrate for an electroluminescence (EL) display panel is manufactured by a photolithography technology, in which patterns are formed on a substrate such as a glass or plastic substrate. At this time, if a scratch or a foreign matter is present on the substrate, the patterns cannot be formed in the most optimum form and adverse effects are resulted. Accordingly, a substrate inspection device is required to use for inspecting defect on a substrate, such as a scratch or a foreign matter.

The substrate inspection device uses an inspection light such as a laser light to irradiate a substrate and receives a reflected or scattered light from the substrate, so as to inspect defect on the substrate such as a scratch or a foreign matter. The inspection of the entire substrate by scanning the substrate with the inspection light is time-consuming. Therefore, the defect on a substrate cannot be inspected with the conventional substrate inspection device in real time in a production line of a glass or plastic substrate or in a production line of a display panel substrate using the glass or plastic substrate. Accordingly, JP Patent Publications No. 2005-164558 discloses a particle inspection method for a glass substrate, in which each glass substrate is scanned with an in-line camera, and the information obtained on particles in a local unit area is quantified, and the statistical value of information of the particle for the whole area of each glass substrate is presented.

The technology reported by JP Patent Publications No. 2005-164558 is to determine if the sum of area of each scanned unit area of the glass substrate is close to and within a tolerance area of one glass substrate (step (e) of claim 1 and S51 of FIG. 4 of the JP Patent Publications No. 2005-164558). When the result is determined as "no", return to the previous step. When the result is determined as "yes", information in the scanned unit areas is collected and added up as the information of one substrate and stored as particle information data for the whole area of the glass substrate (step (f) of claim 1 and S50 of FIG. 4). Thereafter, whether the number of particle of the information on particle for the whole area of the glass substrate is greater than or equal to a predetermined number is determined (S80 of FIG. 4). If the number of particle is greater than or equal to the predetermined number, an alarm is sent (S90 of FIG. 4) to stop the processing.

Therefore, in the technology reported by JP Patent Publications No. 2005-164558, after scanning multiple times to achieve the sum of area of the unit areas being close to the tolerance area of one glass substrate, one particle information for the whole area of the glass substrate is obtained. It is required to repeat again the same number of scanning for obtaining the next particle information. Accordingly, there are problems, for example, the speed of information low, and the identification of problems is delayed.

SUMMARY OF THE INVENTION

The object of the present invention is to enable a rapid inspection of the defects of the in-line substrates.

One aspect of the present invention is described below. A plurality of substrates is sequentially moved while an optical system comprising a light-projecting system and a light-receiving system is moved in a direction orthogonal to the moving direction of each of the plurality of substrates, so as to change a scanned area of each of the plurality of substrates which is scanned with an inspection light having a specific width in the direction orthogonal to the moving direction of each of the plurality of substrates from the light-projecting system; each of the plurality of substrates is irradiated by the inspection light from the light-projecting system; a light from the inspection light reflected or scattered by defects of each of the plurality of substrates is received by the light-receiving system; the defects of each of the plurality of substrates in the scanned area is inspected based on a light intensity received by the light-receiving system; data of the inspected defects of each of the plurality of substrates in the scanned area is stored; and the stored data of the defects of each of the plurality substrates in the scanned area is updated with newly inspected data of defects of each of the plurality of substrates in the same scanned area, and the data of the defects of one substrate of the plurality of substrates are produced based on the data of the defects of each of the plurality of substrates in the scanned area.

A plurality of substrates is sequentially moved while an optical system comprising a light-projecting system and a light-receiving system is moved in a direction orthogonal to the moving direction of each of the plurality of substrates, so as to change the scanned area of each of the plurality of substrates which is scanned with an inspection light having a specific width in the direction orthogonal to the moving direction of each of the plurality of substrates from the light-projecting system; each of the plurality of substrates is irradiated by the inspection light from the light-projecting system; a light from the inspection light reflected or scattered by the defects of each of the plurality of substrates is received by the light-receiving system; the defects of each of the plurality of substrates in the scanned area is inspected based on a light intensity received by the light-receiving system; data of the inspected defects of each of the plurality of substrates in the scanned areas are stored; and the stored data of the defects of each of the plurality of substrates in the scanned area is updated with newly inspected data of the defects of each of the plurality substrates in the same scanned area, and defect data of one substrate of the plurality substrates is produced based on the data of the defects of each of the plurality of substrates in the scanned area. Therefore, the defects of the in-line substrate can be inspected more rapidly.

The other aspect of the present invention is described below. Whether the number of defects of one substrate of the plurality of substrates being within a tolerance value is determined based on the produced defect data of one substrate for each of the plurality of substrates. By determining whether the number of defects of one substrate of the plurality of substrates is within a tolerance value based on the produced defect data of one substrate for each of the plurality of substrates, problems of each substrate can be identified early on when the number of defects of one substrate exceeds the tolerance value.

In order to make the aforementioned and other objects, features and advantages of the present invention comprehensible, a preferred embodiment accompanied with figures is described in detail below.

DESCRIPTION OF EMBODIMENTS

Figure 1:
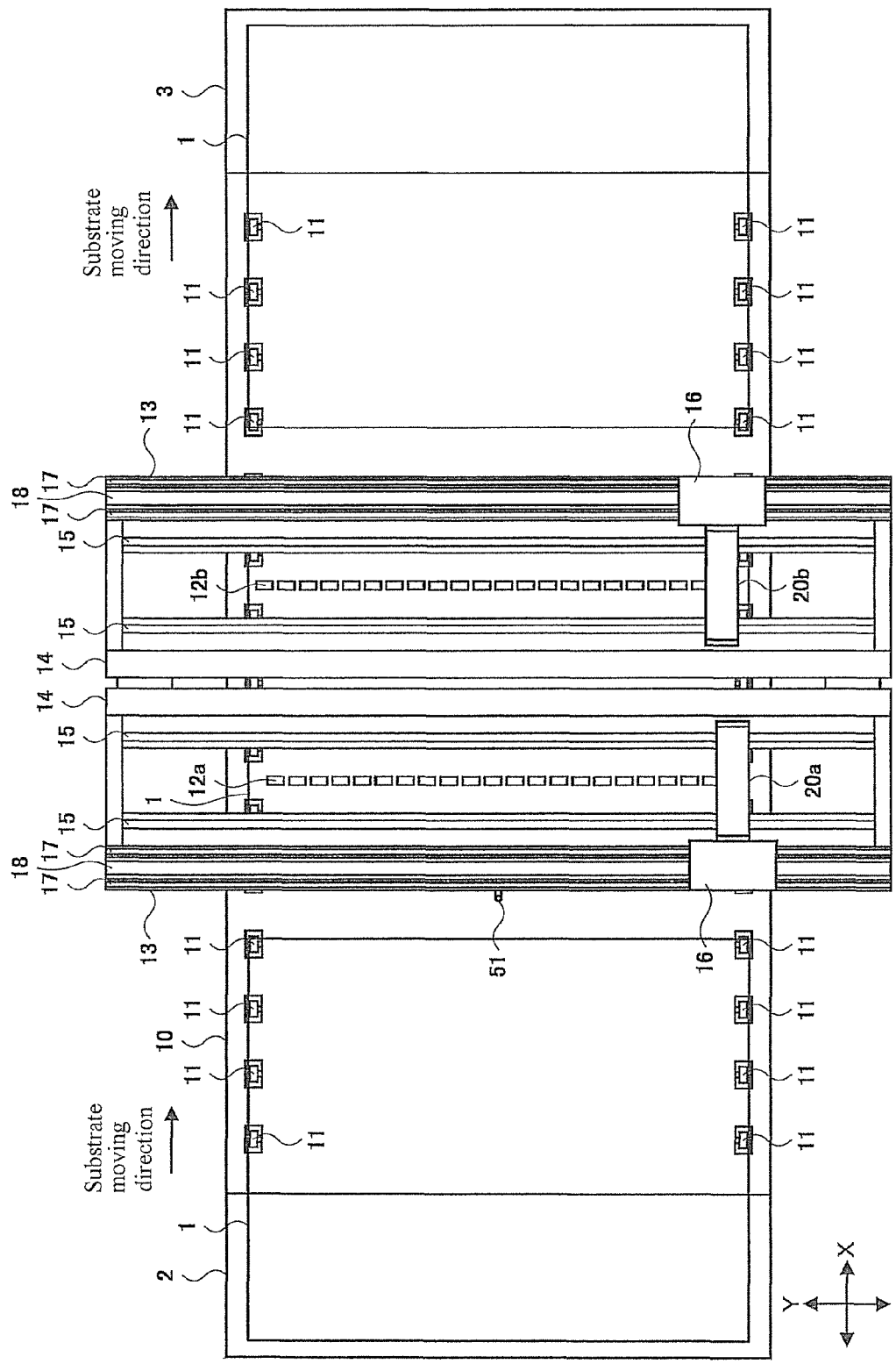
FIG. 1 is a top view of a substrate inspection device according to an embodiment of the present invention.
Figure 2:
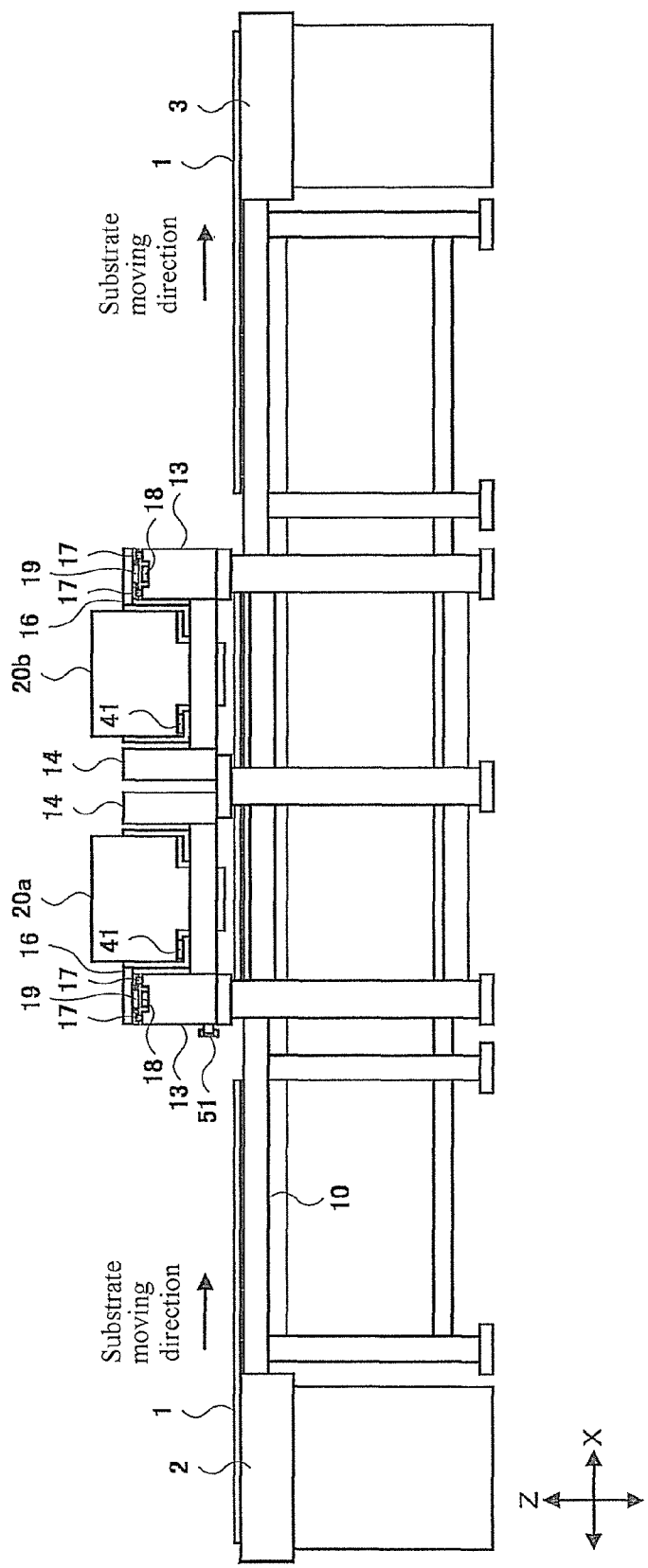
FIG. 2 is side view of a substrate inspection device according to an embodiment of the present invention.

The drawings illustrate embodiments of the present invention and, together with the description, serve to explain the principles of the present invention. FIG. 1 is a top view of a substrate inspection device according to an embodiment of the present invention. FIG. 2 is side view of a substrate inspection device according to an embodiment of the present invention. This embodiment represents an exemplified embodiment, in which a substrate inspection device inspects the defect of a substrate based on a scattered light from the inspection light scattered by the defect on the substrate. The substrate inspection device includes a stage 10, rollers 11, frames 13 and 14, optical system moving means, optical systems 20a and 20b, focus adjustment means 41, a sensor 51 and a control system (will be described below).

Further, XY direction in the illustrated embodiment is only for illustration purposes and is not construed as limiting the present invention. X direction and Y direction can be switched as needed.

Figure 3:
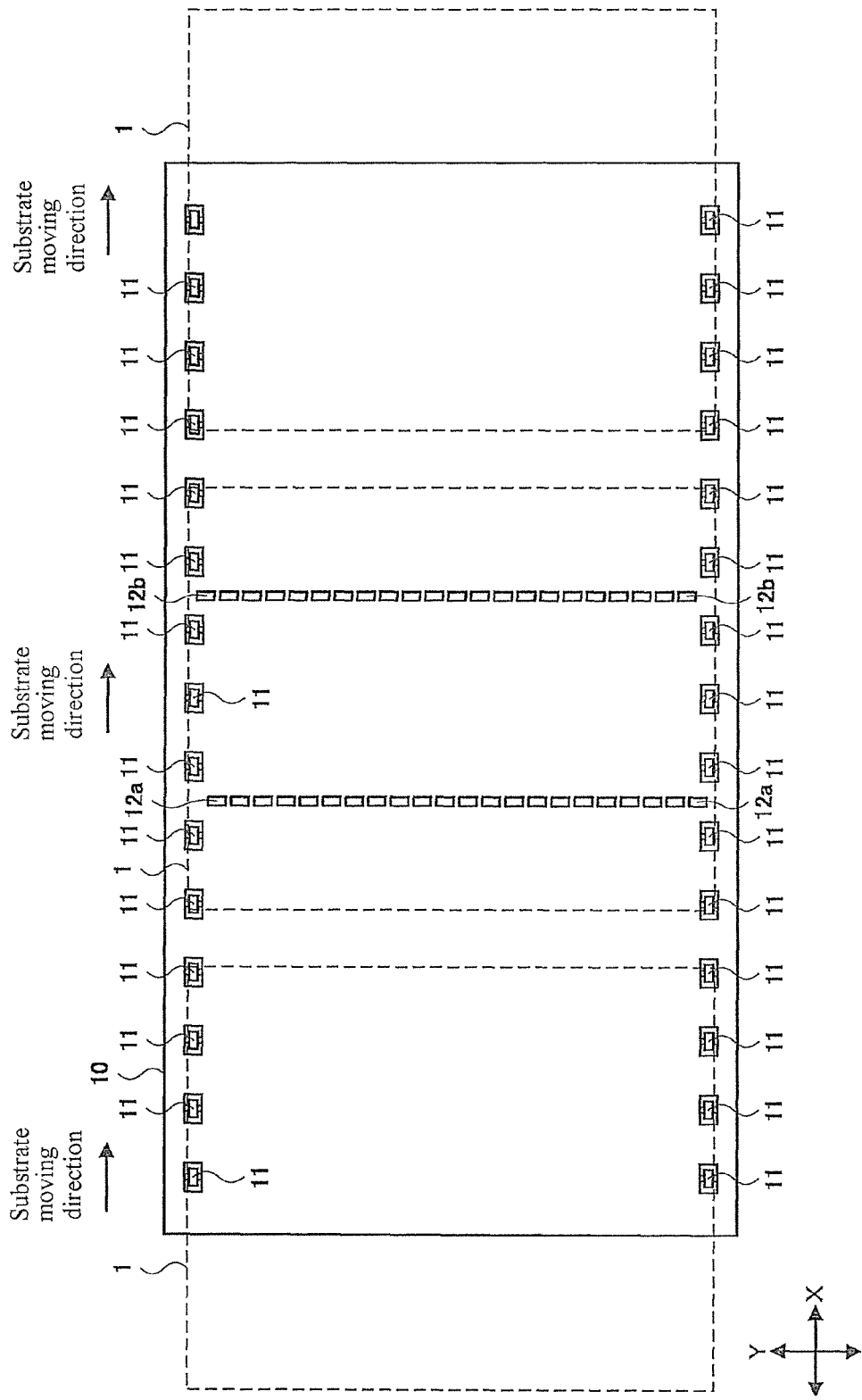
FIG. 3 is a top view of a stage.

In FIG. 1 and FIG. 2, a plurality of in-line substrates 1 as inspection targets is sequentially delivered to the substrate inspection device with an incoming conveyor 2. The substrates 1 exit from the substrate inspection device via an outgoing conveyor 3 after inspection. The stage 10 receives each substrate 1 from the incoming conveyor 2. FIG. 3 is a top view of a stage. The rollers 11 disposed on the stage 10 rotates in contact with the peripheral part of the backside of each substrate 1 (marked by dotted line), so as to sequentially move each substrate 1 in the moving direction of a substrate (X direction) showed as an arrow. The upper surface of the stage 10 has a plurality of air-blowing outlets (not shown), and air is blown to the backside of each substrate 1 from the plurality of air-blowing outlets, so as to suspend each substrate 1 from bending.

In FIG. 1, above the substrates 1 that are moved by the rollers 11, the frames 13 and 14 with a width of greater than or equal to the substrate 1 extending in a direction (Y direction) orthogonal to the moving direction of the substrate (X direction) are disposed cross the substrates 1. On the frames 13 and 14, the optical systems 20a and 20b are disposed in a manner capable of moving along the Y direction with optical system moving means. Further, in this embodiment, two optical systems 20a and 20b are provided for illustration purposes and are not construed as limiting the number of the optical systems of the present invention. One optical system or more than or equal to three optical systems can be disposed as demanded.

Figure 4:
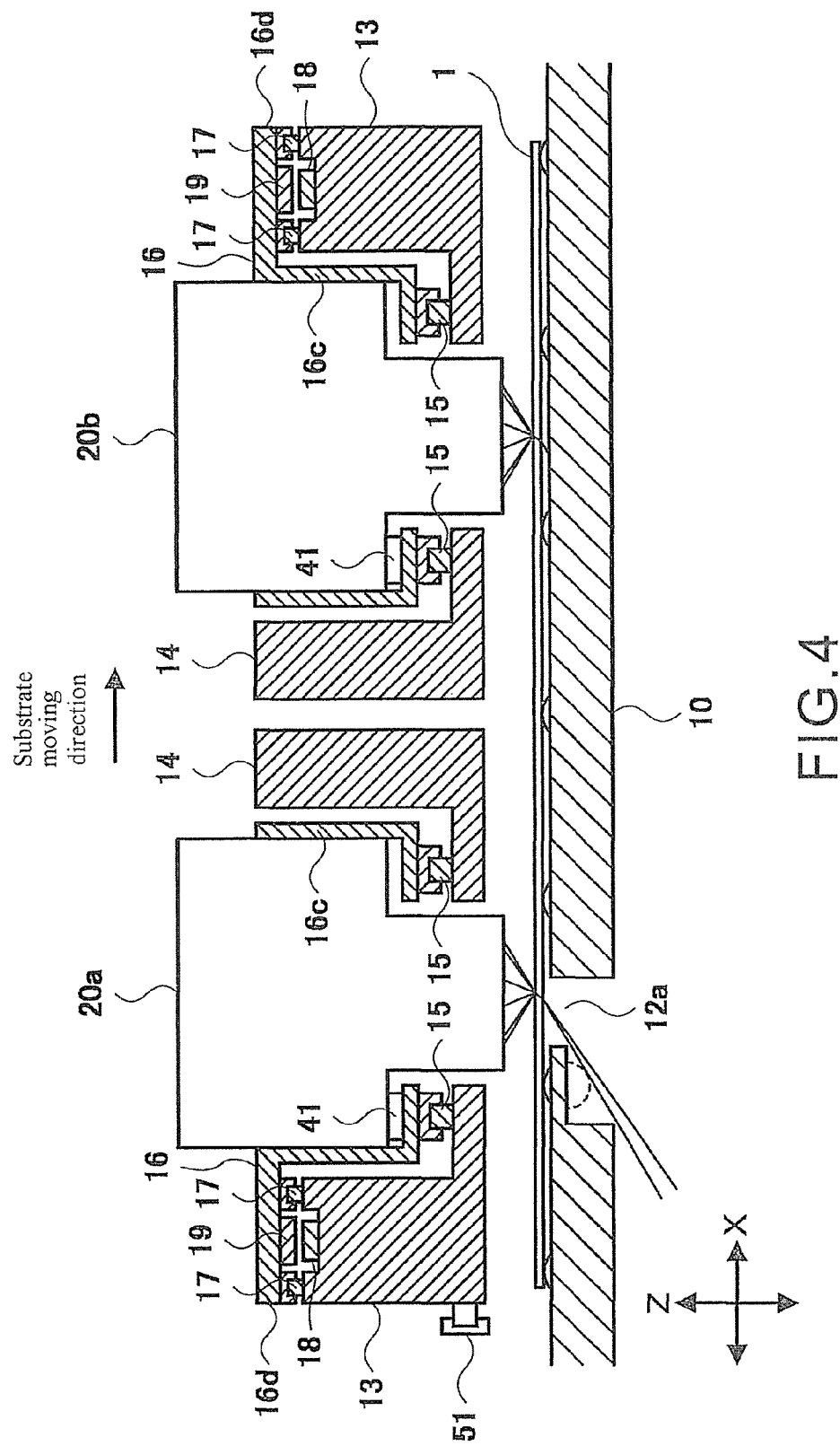
FIG. 4 is a local side view of optical system moving means.

FIG. 4 is a local side view of optical system moving means. The optical system moving means includes guides 15 and 17, a moving stage 16 and a linear motor formed by a magnetic plate 18 and a coil 19. The guides 15 are disposed on the frames 13 and 14 and extended along the depth direction (Y direction) perpendicular to the plane of FIG. 4. The moving stage 16 is disposed on the guides 15. The moving stage 16 has a holding part 16c for holding the optical systems 20a and 20b and an arm part 16d extending horizontally from the holding part 16c disposed thereon. The optical systems 20a and 20b are disposed in the holding part 16c via focus adjustment means 41 (will be described below). Further, the guides 17 are disposed on the frames 13 and extended along the depth direction (Y direction) perpendicular to the figure plane of FIG. 4. The arm parts 16d of the moving stage 16 are disposed on the guides 17. The magnetic plate 18 serving as a stator of the linear motor is installed on the frame 13. The coil 19 serving as a mover of the linear motor is installed on the arm part 16d. When the current flows from an optical system moving control circuit 60 (will be described below) to the coil 19, under the effect of Fleming's left-hand rule, a push force (Lorentz force) is generated on the coil 19 due to the current of the coil 19 and the magnetic field of the magnetic plate 18, so as to move the moving stage 16 along the guides 15 and 17 and to move the optical systems 20a and 20b along the depth direction (Y direction) perpendicular to the figure plane of FIG. 4, which is orthogonal to the substrate moving direction (X direction).

Figure 5:
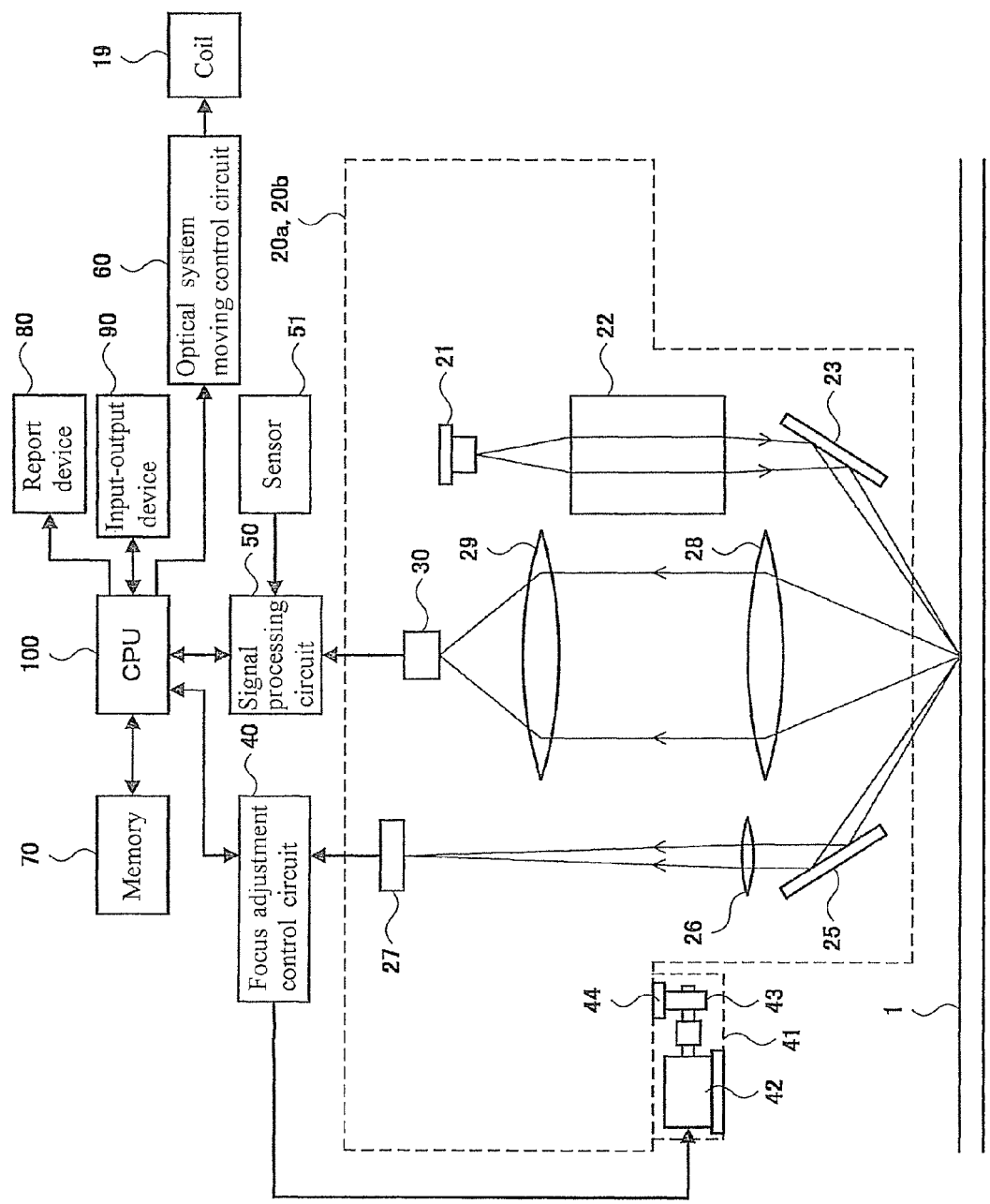
FIG. 5 is a skeleton diagram of an optical system and a control system.

FIG. 5 is a skeleton diagram of an optical system and a control system. Each of the optical systems 20a and 20b includes a light-projecting system, a reflected light inspection system for inspecting the reflected light from the substrate 1, and a light-receiving system for receiving the scattered light from the substrate 1. Further, the control system includes a focus adjustment control circuit 40, a signal processing circuit 50, an optical system moving control circuit 60, a memory 70, a report device 80, an input-output device 90 and a central processing unit (CPU) 100.

Figure 6:
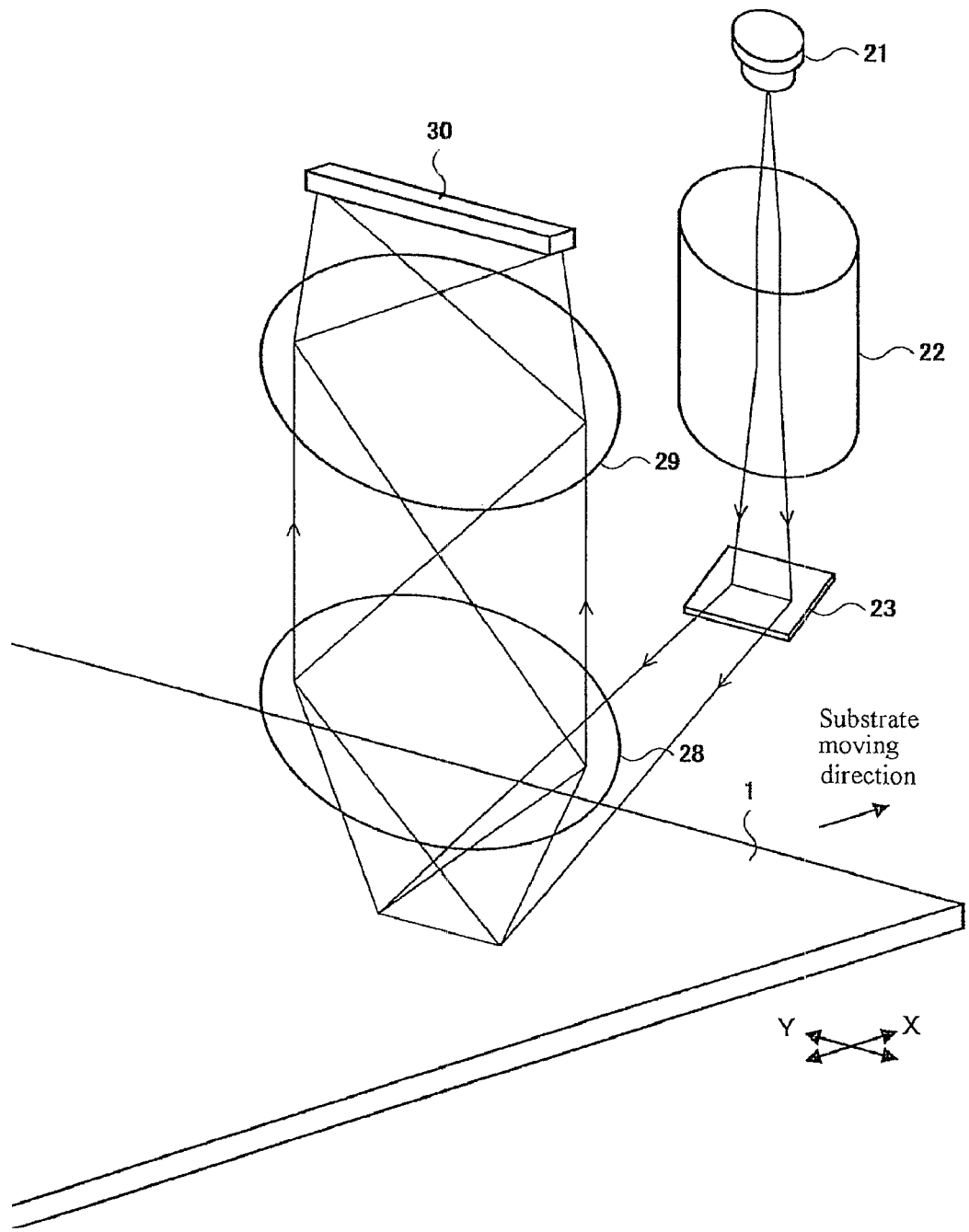
FIG. 6 is a perspective view of a light-projecting system and a light-receiving system of an optical system.

FIG. 6 is a perspective view of a light-projecting system and a light-receiving system of an optical system. The light-projecting system includes a laser source 21, a lens group 22 and a mirror 23. The laser source 21 produces a laser light as an inspection light. The lens group 22 condenses the inspection light produced by the laser source 21, so that the condensed inspection light is expanded in the direction (Y direction) orthogonal to the moving direction of the substrate (X direction), and the expanded inspection light gathers in the substrate moving direction (X direction). The mirror 23 enables the inspection light through the lens group to obliquely irradiate the substrate 1. The inspection light irradiating the substrate 1 gathers on the surface of the substrate 1 in the moving direction of the substrate (X direction), so as to form a light having a specific width in the direction (Y direction) orthogonal to the substrate moving direction (X direction). The inspection light having the specific width emitted from the light-projecting system scans the substrate 1, so as to inspect the defects in the scanned area.

A portion of the inspection light obliquely irradiating the substrate 1 is reflected by the surface of the substrate 1 and another portion of the same passes through the interior of the substrate 1 and emits from the backside of the substrate 1. When a scratch or a foreign matter is present on the surface of the substrate 1, a portion of the inspection light obliquely irradiating the substrate 1 is scattered by the defect and a scattered light is produced.

In FIG. 5, the reflected light inspection system includes a mirror 25, a lens 26 and CCD line sensor 27. The reflected light from the surface of the substrate 1 is incident to the lens 26 via the mirror 25. The lens 26 enables the reflected light from the surface of the substrate 1 for gathering and forming an image on the light-receiving surface of the CCD line sensor 27.

At this time, the light-receiving position of the reflected light on the light-receiving surface of the CCD line sensor 27 is changed as the height of the surface of the substrate 1 varies. The height of the surface of the substrate 1 in FIG. 5 is set as a standard. If the height of the surface of the substrate 1 is lower than the standard, the position irradiated by the inspection light and reflecting the same on the surface of the substrate 1 moves to the left of the figure, and the light-receiving position of the reflected light on the light-receiving surface of the CCD line sensor 27 moves to the right of the figure. On the contrary, if the height of the surface of the substrate 1 is higher than the standard, the position irradiated by the inspection light and reflecting the same on the surface of the substrate 1 moves to the right of the figure, and the light-receiving position of the reflected light on the light-receiving surface of the CCD line sensor 27 moves to the left of the figure.

The CCD line sensor 27 outputs an inspection signal corresponding to the reflected light intensity received by the light-receiving surface to a focus adjustment control circuit 40. The focus adjustment control circuit 40 follows the instruction from the CPU 100 and drives focus adjustment means 41 so as to move the optical systems 20a and 20b based on the inspection signal of the CCD line sensor 27; and thus, the reflected light from the surface of the substrate 1 is received in the center position of the light-receiving surface of the CCD line sensor 27. The focus adjustment means 41 includes a pulse motor 42, a cam 43 and a cam follower 44. The eccentric cam 43 is installed on a revolving spindle of the pulse motor 42. The cam follower 44 is installed in the optical systems 20a and 20b. The focus adjustment control circuits 41 provides a driving pulse to the pulse motor 42 to drive the pulse motor 42, so as to rotate the cam 43, move the optical systems 20a and 20b up and down and adjust the focus position of the optical systems 20a and 20b.

In FIG. 6, the light-receiving system includes a condensing lens 28, an imaging lens 29 and a CCD line sensor 30. The condensing lens 28 condenses the scattered light from the substrate 1. The imaging lens 29 enables the scattered light condensed by the condensing lens 28 to form an image on the light-receiving surface of the CCD line sensor 30. In FIG. 5, the CCD line sensor 30 transforms the inspection signal corresponding to the scattered light intensity received by the light-receiving surface to a digital signal and outputs the digital signal to a signal processing circuit 50.

In FIG. 1 and FIG. 3, on the stage 10, a plurality of openings 12a is disposed on the area irradiated by the inspection light from the light-projecting system of the optical system 20a, and a plurality of openings 12b is disposed on the area irradiated by the inspection light from the light-projecting system of the optical system 20b. The openings 12a and 12b have a length in the direction (Y direction) orthogonal to the moving direction of the substrate (X direction) greater than or equal to the width of the inspection light from the light-projecting system of the optical systems 20a and 20b. The openings 20a and 20b are disposed alternately in different positions. In FIG. 4, the inspection light, emitted from the light-projecting system of the optical system 20a, passed through the inner of the substrate 1 and emitted from the backside of the substrate 1, passes through the openings 12a and arrives to the underside of the stage 10, and is not received by the light-receiving system and the reflected light inspection system of the optical system 20a. The inspection light, emitted from the light-projecting system of the optical system 20b, passed through the inner of the substrate 1 and emitted from the backside of the substrate 1, passes through the openings 12b and arrives to the underside the stage 10, and is not received by the light-receiving system and the reflected light inspection system of the optical system 20b.

Figure 7:
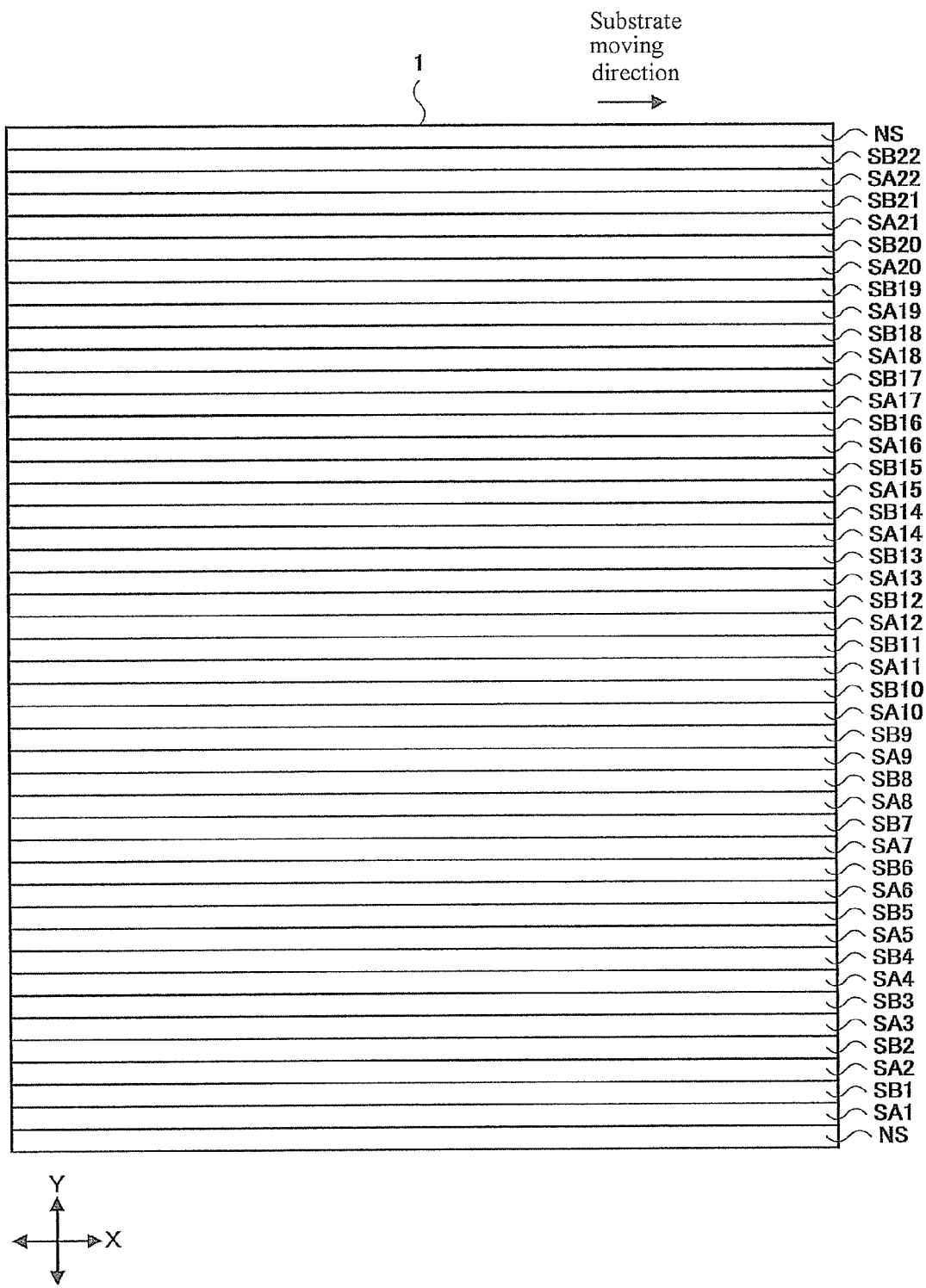
FIG. 7 represents a diagram of scanned areas of a substrate.

In FIG. 5, the optical system moving control circuit 60 follows the instruction from the CPU 100 to provide the current to the coil 19 and to move the optical systems 20a and 20b in the direction (Y direction) orthogonal to the substrate moving of the substrate (X direction), so as to change the scanned areas of the substrates 1, which are scanned with the inspection light having the specific width from the light-projecting system of the optical systems 20a and 20b for each substrate. FIG. 7 represents a diagram of the scanned areas of a substrate. In this embodiment, the inspection area of the substrate 1 is divided into forty-four scanned areas, and two optical systems 20a and 20b respectively scan 22 times. Further, the number of the scanned areas and the number of scanning are not limited thereto, and can be determined properly based on the size of the substrate or the number of the optical systems.

In FIG. 7, the peripheral part of the substrate 1 marked with a symbol NS is the area outside the inspection targets with which the rollers 11 contact, and the areas marked with symbols SA1-SA22 and SB1-SB22 are scanned areas. First, in this embodiment, before the $1^{st}$ substrate 1 arrives to the underside of the sensor 51 (will be described below), the optical system 20a is moved to be above the position where the scanned area SA1 passes, and the optical system 20b is moved to be above the position where the scanned area SB1 passes. Thereafter, for the $1^{st}$ substrate 1, a scanning is performed in the scanned area SA1 with the inspection light from the light-projecting system of the optical system 20a, and another scanning is performed in the scanned area SB1 with the inspection light from the light-projecting system of the optical system 20b.

After the scanning of the $1^{st}$ substrate 1 is finished and before the $2^{nd}$ substrate 1 arrives to the underside of the sensor 51 (will be described below), the optical system 20a is moved to be above the position where the scanned area SA2 passes, and the optical system 20b is moved to be above the position where the scanned area SB2 passes. Thereafter, for the $2^{nd}$ substrate 1, a scanning is performed in the scanned area SA2 with the inspection light from the light-projecting system of the optical system 20a, and another scanning is performed in the scanned area SB2 with the inspection light from the light-projecting system of the optical system 20b. The above-mentioned steps are repeated. For the $22^{nd}$ substrate 1, a scanning is performed in the scanned area SA22 with the inspection light from the light-projecting system of the optical system 20a, and another scanning is performed in the scanned area SB22 with the inspection light from the light-projecting system of the optical system 20b.

After the scanning of the $22^{nd}$ substrate 1 is finished, the $23^{rd}$ to $44^{th}$ substrates 1 are scanned in the same way as the $1^{st}$ to $22^{nd}$ substrates 1. Alternately, after the $23^{rd}$ substrate 1 is scanned in the same way as the $22^{nd}$ substrate 1, the optical systems 20a and 20b are moved to be opposite to the original direction, and the 24$^{th}$ to 44$^{th}$ substrates 1 are scanned in the same way as the 21$^{st}$ to 1$^{st}$ substrates 1. The substrates 1 after the 44$^{th}$ substrate 1 are scanned in the same way.

In FIG. 1 and FIG. 2, the sensor 51 inspects the side edges of the substrates 1 moved by the rolls 11 in the moving direction of the substrate and outputs the inspection signal to the signal processing circuit 50 of FIG. 5. In FIG. 5, the signal processing circuit 50 processes the digital signal from the CCD line sensor 30, inspects the defects of the substrates 1 in the scanned areas with different ranks corresponding to the predetermined sizes, and inspects the positions of the inspected defects in the scanned areas in the direction (Y direction) orthogonal to the substrate moving direction (X direction). Thereafter, the signal processing circuit 50 inspects the positions of the inspected defects in the moving direction of the substrate (X direction) based on the elapsed time after the sensor 51 outputs the inspection signal. The signal processing circuit 50 outputs information of the inspected defects to the CPU 100.

By the control of the CPU 100, the memory 70 stores the information of the defects of the substrates 1 in the scanned areas inspected by the signal processing circuit 50 for each scanned area. The report device 80 reports with the control of the CPU 100. The input-output device 90 inputs a line stop instruction (will be described below), and then outputs the defect information and the determined result with the control of the CPU 100.

Figure 8:
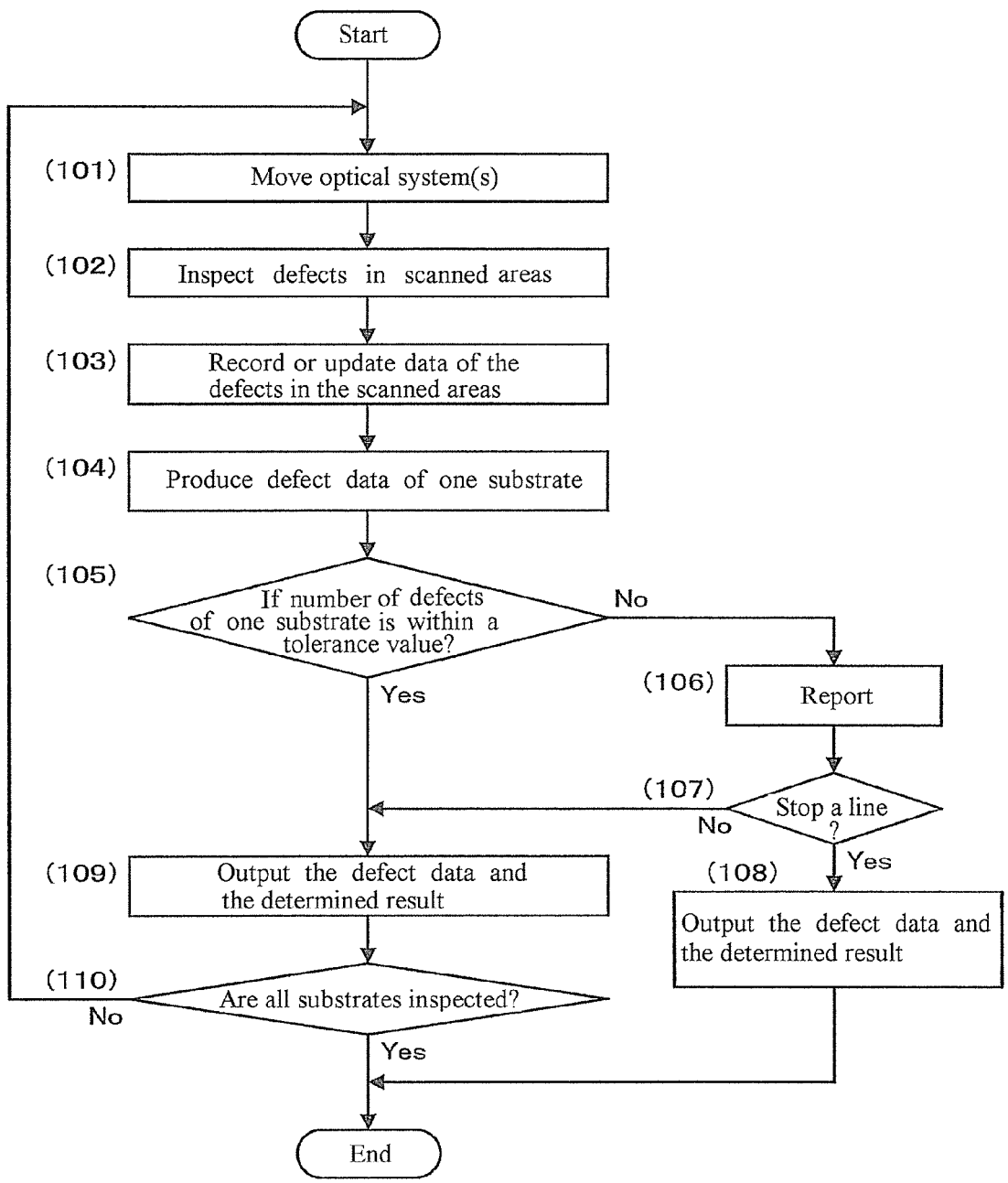
FIG. 8 is a flow chart of a substrate inspection method according to an embodiment of the present invention.

FIG. 8 is a flow chart of a substrate inspection method according to an embodiment of the present invention. First, the CPU 100 sends an instruction to the optical system moving control circuit 60 to move the optical systems 20a and 20b. The optical system moving control circuit 60 follows the instruction from the CPU 100 and supplies a current to the coil 19, so as to move the optical systems 20a and 20b to be above the position where each scanned area passes (step 101). The substrates 1 are moved by the rolls 11, and the signal processing circuit 50 processes the digital signal from the CCD line sensor 30, so as to inspect defects of the substrates 1 in scanned areas (step 102).

Thereafter, the CPU 100 controls the memory 70, so as to store the data of the inspected defects of the substrates for each scanned area and update the stored data of the defects of the substrates 1 in the scanned areas in the memory 70 with data of defects of the substrates 1 newly obtained by the signal processing circuit 50 for each substrate (step 103). Afterwards, the CPU 100 produces the defect data of one substrate based on the data of the defects of the substrates 1 in a plurality of scanned areas stored in the memory 70 (step 104).

Further, the CPU 100 determines whether the number of defects of one substrate is within a tolerance value based on the produced defect data of one substrate for each substrate (step 105). The determination can be performed according to the degree of the defects, which corresponds to the sizes of the defects, or performed with all the defects in one substrate without concerning the sizes of the defects. When the number of defects of one substrate is within the tolerance value, go to step 109. When the number of defects of one substrate exceeds the tolerance value, the CPU 100 controls the report device 80 to report that the number of defects of one substrate has exceeded the tolerance value to a line manager or line control equipment (step 106). Then, the CPU 100 determines if the line manager or the line control equipment inputs a line stop instruction to the input-output device 90 (step 107). When the line stop instruction is not input, go to step 109. When the line stop instruction is input, the CPU 100 controls the input-output device 90 to output the defect data and the determined result (step 108), and to stop the processing.

Thereafter, the CPU 100 controls the input-output device 90 to output the defect data and the determined result for each substrate (step 109). The output of the defect data, such as showing via a monitor display or printing a map if the sizes of the defects and the positions thereof with a printer, or showing via a monitor display the degree of the defects, which corresponds to the sizes of the defects, or printing the number of defects of each scanned area and the number of defects of one substrate 1 with a printer. Afterwards, the CPU 100 determines if all substrates have been inspected (step 110). If not all substrates have been inspected, go back to step 101. If all substrates have been inspected, the processing terminates.

According to the above-mentioned embodiment, the data of the inspected defects of the substrates are stored for each scanned area, and the stored data of the defects of the substrates in the scanned areas are updated with newly inspected data of the defects of the substrates for each substrate (step 103). The defect data of one substrate are produced based on the data of the defects of the substrates in a plurality of scanned areas (step 104). Accordingly, for each substrate, the defect data of one substrate are obtained, and the defects of the in-line substrates can be inspected more rapidly.

Further, according to the above-mentioned embodiment, whether the number of defects of one substrate being within a tolerance value is determined based on the produced defect data of one substrate for each substrate (step 105). The problems of each substrate can be identified in early stage when the number of defects of one substrate exceeds the tolerance value.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

What is claimed is:

1. A substrate inspection device, comprising:
   a substrate moving means, sequentially moving a plurality of substrates;
   an optical system, comprising a light-projecting system and a light-receiving system, wherein the light-projecting system irradiates the plurality of substrates moved by the substrate moving means with an inspection light having a specific width in a direction orthogonal to a moving direction of each of the plurality of substrates, and the light-receiving system receives a light from the inspection light reflected or scattered by defects of each of the plurality of substrates;
   an optical system moving means, moving the optical system in the direction orthogonal to the moving direction of each of the plurality of substrates, so as to change a scanned areas of each of the plurality of substrates which is scanned with the inspection light from the light-projecting system;
   a processing means, inspecting the defects of each of the plurality of substrates in the scanned area based on a light intensity received by the light-receiving system;
   a storage means, storing data of the defects of each of the plurality of substrates in the scanned area inspected by the processing means; and
   a control means, controlling the storage means and updating the data of the defects of each of the plurality of substrates in the scanned area stored by the storage means with data of the defects of each of the plurality of substrates newly obtained by the processing means in the same scanned area, and producing defect data of one substrate of the plurality of substrates based on the data of the defects of each of the plurality of substrates in the scanned area stored by the storage means.

2. The substrate inspection device of claim 1, wherein the control means determines whether a number of the defects of the one substrate is within a tolerance value based on the produced defect data of the one substrate for each of the plurality of substrates.

3. A substrate inspection method, comprising:

sequentially moving a plurality of substrates while moving an optical system comprising a light-projecting system and a light-receiving system in a direction orthogonal to a moving direction of each of the plurality of substrates, so as to change a scanned area of each of the plurality of substrates which is scanned with an inspection light having a specific width in the direction orthogonal to the moving direction of each of the plurality of substrates from the light-projecting system;

irradiating each of the plurality of substrates with the inspection light from the light-projecting system;

receiving a light from the inspection light reflected or scattered by defects of each of the plurality substrates with the light-receiving system;

inspecting the defects of each of the plurality substrates in the scanned area based on a light intensity received by the light-receiving system;

storing data of the inspected defects of each of the plurality of substrates in the scanned area; and updating the stored data of the defects of each of the plurality of substrates in the scanned area with newly inspected data of the defects of each of the plurality of substrates in the same scanned area, and producing defect data of one substrate of the plurality of substrates based on the data of the defects of each of the plurality of substrates in the scanned area.

4. The substrate inspection method of claim 3, wherein whether a number of the defects of the one substrate being within a tolerance value is determined based on the produced defect data of the one substrate for each of the plurality of substrates.

* * * * *